US008007540B2

(12) United States Patent
Robertson

(10) Patent No.: US 8,007,540 B2
(45) Date of Patent: *Aug. 30, 2011

(54) URETERAL STENT WITH END-EFFECTOR

(75) Inventor: David W. Robertson, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1037 days.

This patent is subject to a terminal disclaimer.

(21) Appl. No.: 11/229,611

(22) Filed: Sep. 20, 2005

(65) Prior Publication Data

US 2006/0015190 A1   Jan. 19, 2006

Related U.S. Application Data

(63) Continuation of application No. 10/123,808, filed on Apr. 16, 2002, now Pat. No. 6,949,125.

(51) Int. Cl.
*A61F 2/04* (2006.01)
*A61M 37/00* (2006.01)
(52) U.S. Cl. ................. 623/23.64; 623/23.66; 604/8
(58) Field of Classification Search ........... 623/23.66, 623/23.64, 23.68, 23.7; 604/8
See application file for complete search history.

(56) References Cited

U.S. PATENT DOCUMENTS

| 3,890,977 | A | 6/1975 | Wilson |
| 4,212,304 | A | 7/1980 | Finney |
| 4,307,723 | A | 12/1981 | Finney |
| 4,334,327 | A | 6/1982 | Lyman et al. |
| 4,531,933 | A | 7/1985 | Norton et al. |
| 4,553,959 | A | 11/1985 | Hickey et al. |
| 4,568,338 | A | 2/1986 | Todd |
| 4,575,371 | A * | 3/1986 | Nordqvist et al. ....... 604/103.07 |
| 4,610,657 | A | 9/1986 | Densow |
| 4,643,716 | A | 2/1987 | Drach |
| 4,671,795 | A | 6/1987 | Mulchin |
| 4,713,049 | A | 12/1987 | Carter |
| 4,738,667 | A | 4/1988 | Galloway |

(Continued)

FOREIGN PATENT DOCUMENTS

EP    0 287 763    10/1988

(Continued)

OTHER PUBLICATIONS

Hepperlen, T., et al., Self-Retained Internal Ureteral Stents: A New Approach, The Journal of Urology, 1978, vol. 119, pp. 731-734.

(Continued)

*Primary Examiner* — Suzette J Gherbi

(57) ABSTRACT

A system and related methods for maintaining the patentcy of the ureter comprising a pusher tube having a pusher tube lumen and an inflate lumen disposed within a wall of the pusher tube and a urinary stent having a proximal and distal portions with an elongated body portion therebetween configured to fit the ureter of the patient and defining a lumen. The system further includes an end-effector that may comprise an inflatable balloon positioned at the proximal portion of the urinary stent for retaining the proximal portion in the urinary bladder. At the distal portion, a retention end-piece is positioned for retaining the distal portion of the stent in the renal pelvis. The end-effector and the retention end-piece of the stent maintain the elongated body portion in situ. The end-effector may also include an inflatable balloon and may contain pharmaceutical or biologic agents for controlled release into the bladder.

25 Claims, 5 Drawing Sheets

U.S. PATENT DOCUMENTS

| | | | |
|---|---|---|---|
| 4,762,128 | A | 8/1988 | Rosenbluth |
| 4,787,884 | A | 11/1988 | Goldberg |
| 4,790,809 | A | 12/1988 | Kuntz |
| 4,790,810 | A | 12/1988 | Pugh, Jr. et al. |
| 4,813,925 | A | 3/1989 | Anderson, Jr. et al. |
| 4,820,262 | A | 4/1989 | Finney |
| 4,846,814 | A | 7/1989 | Ruiz |
| 4,874,360 | A | 10/1989 | Goldberg et al. |
| 4,887,996 | A | 12/1989 | Bengmark |
| 4,913,683 | A | 4/1990 | Gregory |
| 4,931,037 | A | 6/1990 | Wetterman |
| 4,950,228 | A | 8/1990 | Knapp, Jr. et al. |
| 4,957,479 | A | 9/1990 | Roemer |
| 4,990,133 | A | 2/1991 | Solazzo |
| 5,019,102 | A | 5/1991 | Hoene |
| 5,049,132 | A * | 9/1991 | Shaffer et al. ............ 604/101.02 |
| 5,052,998 | A | 10/1991 | Zimmon |
| 5,078,684 | A | 1/1992 | Yasuda |
| 5,078,736 | A | 1/1992 | Behl |
| 5,112,306 | A | 5/1992 | Burton |
| 5,116,309 | A | 5/1992 | Coll |
| 5,141,502 | A | 8/1992 | Macaluso, Jr. |
| 5,176,625 | A | 1/1993 | Brisson |
| 5,176,626 | A | 1/1993 | Soehendra |
| 5,221,253 | A | 6/1993 | Coll |
| 5,224,953 | A | 7/1993 | Morgentaler |
| 5,234,456 | A | 8/1993 | Silvestrini |
| 5,246,445 | A | 9/1993 | Yachia et al. |
| 5,269,802 | A | 12/1993 | Garber |
| 5,282,784 | A | 2/1994 | Willard |
| 5,346,467 | A | 9/1994 | Coll |
| 5,354,263 | A | 10/1994 | Coll |
| 5,364,340 | A | 11/1994 | Coll |
| 5,380,270 | A | 1/1995 | Ahmadzadeh |
| 5,401,257 | A | 3/1995 | Chevalier, Jr. et al. |
| 5,411,551 | A | 5/1995 | Winston et al. |
| 5,441,515 | A | 8/1995 | Khosravi et al. |
| 5,496,271 | A * | 3/1996 | Burton et al. ................... 607/27 |
| 5,514,176 | A | 5/1996 | Bosley, Jr. |
| 5,520,697 | A | 5/1996 | Lindenberg et al. |
| 5,531,741 | A | 7/1996 | Barbacci |
| 5,545,135 | A | 8/1996 | Iacob et al. |
| 5,599,291 | A | 2/1997 | Balbierz et al. |
| 5,624,395 | A | 4/1997 | Mikhail et al. |
| 5,647,843 | A | 7/1997 | Mesrobian et al. |
| 5,681,274 | A | 10/1997 | Perkins et al. |
| 5,716,393 | A | 2/1998 | Lindenberg et al. |
| 5,795,319 | A | 8/1998 | Ali |
| 5,857,998 | A | 1/1999 | Barry |
| 6,045,568 | A | 4/2000 | Igaki et al. |
| 6,087,396 | A | 7/2000 | Roberts |
| 6,102,848 | A | 8/2000 | Porter |
| 6,139,535 | A | 10/2000 | Greelis et al. |
| 6,168,602 | B1 | 1/2001 | Ryan |
| 6,183,461 | B1 | 2/2001 | Matsuura et al. |
| 6,302,917 | B1 * | 10/2001 | Dua et al. .................... 623/23.68 |
| 6,524,268 | B2 * | 2/2003 | Hayner et al. ..................... 604/8 |
| 6,656,146 | B1 * | 12/2003 | Clayman et al. .................. 604/8 |
| 6,921,378 | B2 * | 7/2005 | O'Keefe et al. ................... 604/9 |
| 6,949,125 | B2 * | 9/2005 | Robertson .................... 623/23.7 |
| 2001/0034470 | A1 * | 10/2001 | Whalen et al. .................. 600/30 |
| 2002/0082551 | A1 * | 6/2002 | Yachia et al. ............ 604/103.01 |
| 2005/0080399 | A1 * | 4/2005 | Bolmsjo et al. ............... 604/509 |

FOREIGN PATENT DOCUMENTS

| | | |
|---|---|---|
| WO | WO 00/66032 | 11/2001 |
| WO | WO 01/89415 A2 | 11/2001 |
| WO | WO0228465 A1 * | 4/2002 |

OTHER PUBLICATIONS

Camacho, M.F., et al., Double-Ended Pigtail Ureteral Stent: Useful Modification to Single End Ureteral Stent, Urology, May 1979, vol. 13, No. 5, pp. 516-520.

Mardis, H.K., et al., Double Pigtail Ureteral Stent, Urology, Jul. 1979, vol. 14, No. 1, pp. 23-26.

Mardis, H.K., et al., Polyethylene Double-Pigtail Ureteral Stents, Urologic Clinics of North America, Feb. 1982, vol. 9. No. 1 pp. 95-101.

Stables, D., Percutaneous Nephrostomy: Techniques, Indications, and Results, Urologic Clinics of North America, Feb. 1982, vol. 9, No. 1, pp. 15-29.

Minkov, N., et al., Our Experience in the Application of the Biocompatible Indwelling Ureteral Stents, International Urology and Nephrology, 1986, vol. 18, No. 4, pp. 403-409.

Mardis, H.K., Evaluation of Polymeric Materials for Endourologic Devices, Seminars in Interventional Radiology, Mar. 1987, vol. 4, No. 1, pp. 36-45.

Birch, B.R.P., et al., Tethered Ureteric-Stents—A Clinical Assessment, British Journal of Urology, 1988, vol. 62, pp. 409-411.

Mardis, H.K., et al., Ureteral Stents, Urologic Clinics of North America, 1988, vol. 15, No. 3, pp. 471-479.

Bard Urological Division—Product Catalog, 1990.

Cook Urological—Urological Surgical Products, 1990, pp. 176-228.

Mardis, H.K., et al., Ureteral Stents: Use and Complications, Problems in Urology, Jun. 1992, vol. 6, No. 2, pp. 296-306.

Mardis, H.K., et al., Comparative Evaluation of Materials Used for Internal Ureteral Stents, Journal of Endourology, 1993, vol. 7, No. 2, pp. 105-115.

Culkin, D.J., Complications of Ureteral Stents, Infections in Urology, Sep. 1996, pp. 139-143.

Mardis, H.K., Self-Retained Internal Ureteral Stents: Use and Complications, AUA Update Series, Lesson 29, 1997, vol. 16, pp. 226-232.

International Search Report for International Patent Application No. PCT/US03/10766, 7 pages.

* cited by examiner

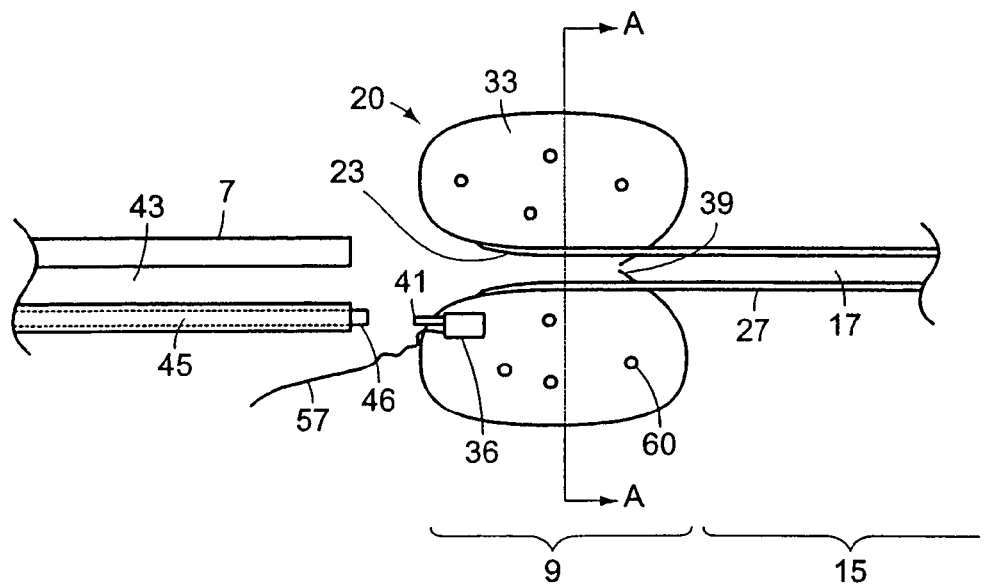
FIG. 2
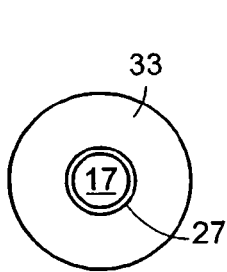 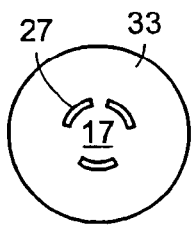 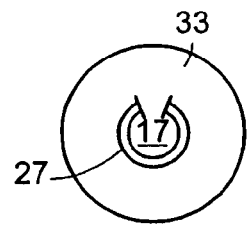 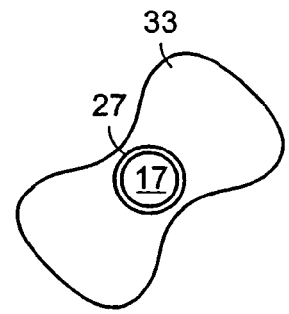
FIG. 3A  FIG. 3B  FIG. 3C  FIG. 3D
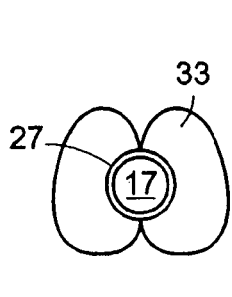 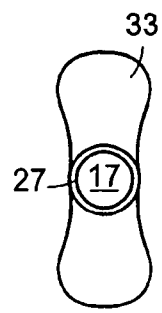 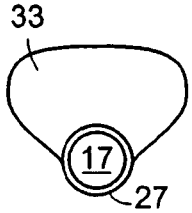 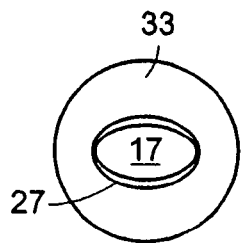
FIG. 3E  FIG. 3F  FIG. 3G  FIG. 3H

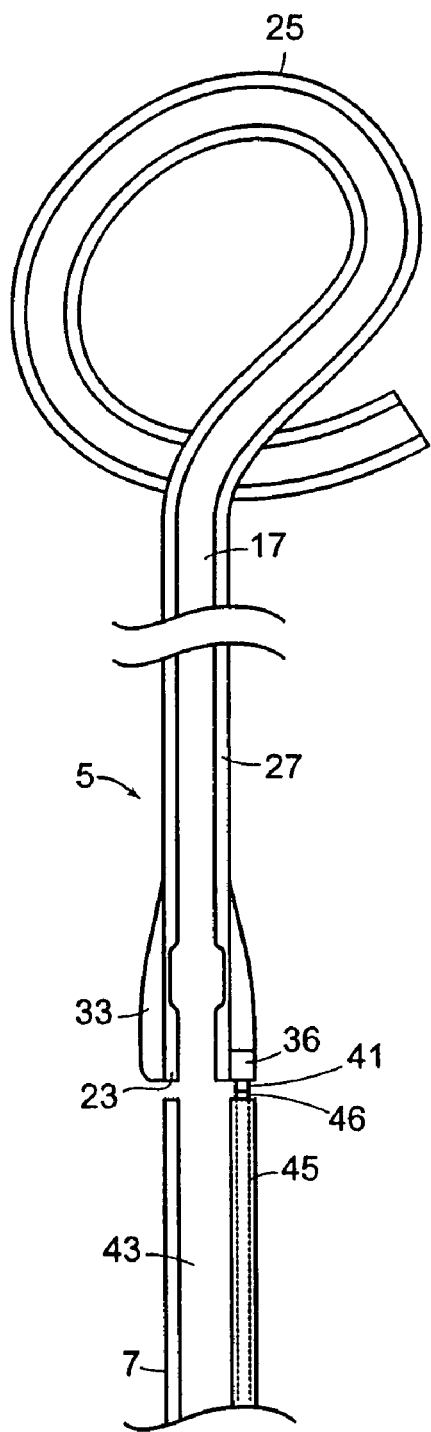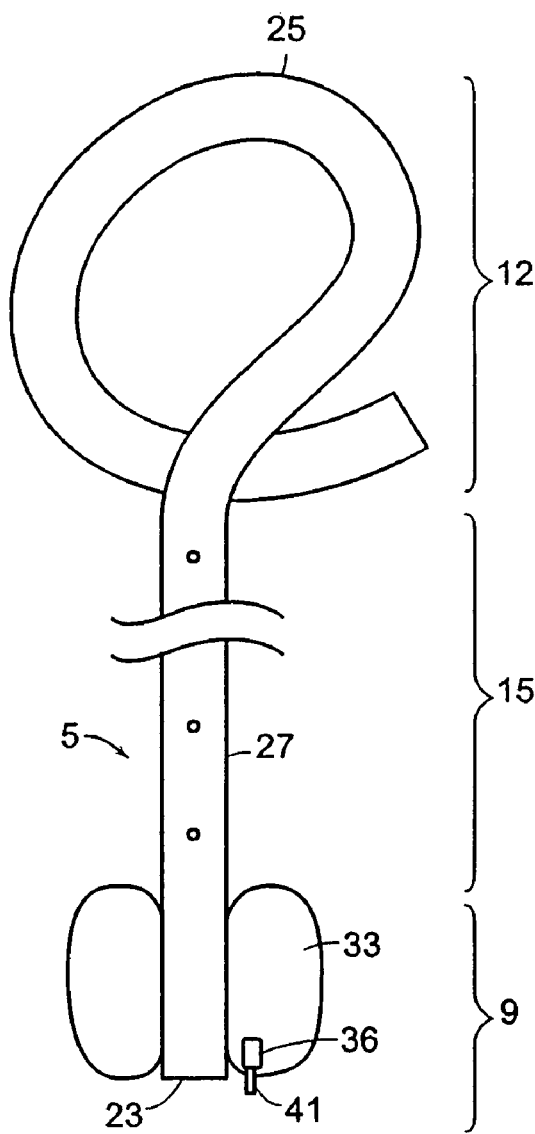
FIG. 5A
FIG. 5B

URETERAL STENT WITH END-EFFECTOR

This application is a continuation application of U.S. patent application Ser. No. 10/123,808, filed Apr. 16, 2002, and entitled URETERAL STENT WITH END-EFFECTOR AND RELATED METHODS, now U.S. Pat. No. 6,949,125, the entire content of which is hereby incorporated by reference.

FIELD OF THE INVENTION

This invention generally relates to stents and more particularly to ureteral stents.

BACKGROUND

Ureteral stents are used to create a pathway for urinary drainage from the kidney to the bladder in patients with ureteral obstruction or injury or to protect the integrity of the ureter in a variety of surgical manipulations. A number of clinical conditions can produce interruption in urine flow including, for example, intrinsic obstruction of the ureter due to tumor growth, stricture or stones, compression of the ureter due to extrinsic tumor growth, stone fragment impactation in the ureter following extracorporeal shock wave lithotripsy (ESWL), and ureteral procedures such as ureteroscopy and endopyelotomy. Stents may be used to treat or avoid obstructions of the ureter (such as ureteral stones or ureteral tumors) that disrupt the flow of urine from the corresponding kidney to the urinary bladder. Serious obstructions of the urinary tract may cause urine to back up into the kidney, threatening renal function. Ureteral stents may also be used after endoscopic inspection of the ureter. The stent may be placed in the ureter to facilitate the flow of urine from the kidney to the bladder and to enable the ureter to heal.

Ureteral stents typically are tubular in shape, terminating in two opposing ends: a kidney distal end and a urinary bladder proximal end. One or both of the ends of the stent may be coiled in a pigtail spiral or J-shape to prevent the upward and/or downward migration of the stent in the lumen of the ureter due to, for example, day-to-day physical activity of the patient. A kidney end coil is designed to retain the stent within the renal pelvis and to prevent stent migration down the ureter. A urinary bladder end coil is positioned in the bladder and is designed to prevent stent migration upward toward the kidney. The bladder end-coil is also used to aid in retrieval and removal of the stent.

A ureteral stent assists in the flow of urine from the kidney to the urinary bladder. The region known as the trigone is an area that surrounds the ureteral orifices at the insertion of the ureters into the bladder and extends to the bladder neck at the urethral outlet of the bladder. The trigone has greater pain sensation relative to other regions of the bladder wall and is a major source of patient discomfort when the typical indwelling stent is in contact with this region of the bladder.

Ureteral stents may be introduced to the body either percutaneously in an antigrade fashion, using for example, an adaptation of the Seldinger technique, or cystoscopically in a retrograde fashion. The stents positioned in the bladder through a cystoscope are passed into the ureter using direct vision through the endoscope positioned in the bladder. For placing the stent, there are two conventional techniques. A guidewire of sufficient stiffness and maneuverability is inserted into the ureter under endoscopic guidance. When access past the ureteral obstruction of the kidney is achieved, the stent is introduced to the ureter over the wire by a pusher catheter acting on the trailing or proximal edge of the stent.

The second conventional placement method for ureteral stents omits the prior step of placing a guidewire and may be used where no large obstruction is present. In this method, the guidewire is inserted through the stent only until it is flush with or within the tip the stent. A pusher catheter is again inserted behind the stent on the guidewire and is locked to the guidewire with a locking hub (e.g., SPEED-LOK® product available from Boston Scientific Corporation, Natick, Mass.). The assembly is then pushed by the pusher catheter acting on the proximal end of the stent to enter the cystoscope and then the ureter.

Ureteral stents, particularly the portion positioned in the ureter and the bladder, may produce adverse effects including hemorrhage, a continual urge to urinate, flank pain accompanying reflux of urine back up the ureter due to retrograde pressure when voiding, and chronic trigone and flank pain. Chronic trigone irritation resulting from contact by the bladder anchoring features of the stent or resulting from intraoperative trauma inflicted from passage of the device in the ureter.

Flank pain may be caused from typical ureteral stents during urinary voiding. On the initiation of voiding the bladder wall muscles contract causing the pressure inside the bladder to rise. Because a typical indwelling ureteral stent holds the ureteral orifice open, this pressure is transmitted to the kidney causing the patient to experience flank pain. Attempts to mitigate some of these problems associated with ureteral stents include administering systemic pharmaceuticals such as anti-spasmodic drugs which may present additional undesirable side effects. In general, ureteral stents may cause or contribute to significant patient discomfort and serious medical problems.

SUMMARY OF THE INVENTION

It is therefore an object of this invention to provide a more comfortable ureteral drainage device providing an end-effector, including a balloon at the proximal portion of a stent that will be less irritating that a typical indwelling stent. When positioned within the ureter of a mammal, the device assists in reducing fluid retention by facilitating the drainage of urine from the kidney into the urinary bladder while minimizing patient discomfort. In general, one aspect of the invention described herein relates to a system for introducing a ureteral stent into a patient.

It is a further object of the invention to reduce pain due to the reflux of pressure up the stent by providing a uni-directional valve at the proximal portion that serves to substantially occlude the lumen of the stent during increases in bladder pressure.

It is a further object of this invention to provide a ureteral stent system that facilitates easy implantation and removal from a patient.

It is a further object of this invention to provide a stent for delivering a pharmaceutical agent into the bladder of a patient at a controlled rate.

It is a further object of this invention to prevent or reduce the reflux of urine back up the ureter due to retrograde pressure during voiding.

In a first aspect the invention is a ureteral stent having proximal and distal ends, and an elongated body portion dimensioned and configured to fit the ureter of the patient and defining a lumen. In one embodiment of the invention, the proximal end of the ureteral stent includes a proximal end-effector positioned at the proximal portion of the urinary stent for retaining the proximal portion in the urinary bladder. In a particular embodiment of the invention, the proximal end-effector includes an inflatable balloon. At the distal end, a retention end-piece is positioned for retaining the distal portion of the stent in the renal pelvis, wherein the proximal end-effector and the retention end-piece maintain the elongated body portion of the ureteral stent in situ.

In one embodiment of this aspect of the invention, the retention end-piece includes a substantially planar spiral, or alternatively, a substantially helical coil. In another embodiment of the invention, the proximal end-effector includes a self-sealing valve, or a bi-directional valve. In another embodiment, the proximal end-effector contains a reservoir for storing and delivering a solution contained therein. The proximal end-effector may also include a connector for reversibly receiving a pusher tube. In a particular embodiment, the balloon includes a lumen disposed therethrough, a self-sealing valve, and a retrieval suture attached to the valve to effect remote release of the balloon contents and removal of the stent.

In another embodiment of the stent according to the invention, the lumen through the balloon collapses when a predetermined external pressure is exerted on the balloon such as during urinary voiding. The balloon may be formed on the wall of the stent such that when it is inflated in situ the balloon everts over the shaft attachment and forms an attached toroid. This configuration limits direct contact of the balloon with the ureteral orifice, seals the ureteral orifice from bladder pressure, and allows the stent to move in relation to the balloon to adjust to variations in ureteral length due to patient respiration and movement.

In another aspect, the invention is a system for introducing a urinary stent into the body of a patient. The system includes a pusher tube having a pusher tube lumen and an inflate lumen disposed within a wall of the pusher tube. The system further includes a urinary stent having a proximal end, a distal end, and an elongated body portion configured to fit the ureter of the patient and defining a lumen therebetween. The system further includes a balloon positioned at the proximal end of the urinary stent (that is deflated for ease of passage through the urethra during placement and for retaining the proximal end in the urinary bladder after inflation) and a retention end-piece positioned at the distal end of the stent for retaining the distal end of the stent in the renal pelvis, wherein the balloon and the retention end-piece maintain the elongated body portion in situ. In one embodiment, the system according to the invention may further include a connector for reversibly receiving the pusher tube.

In another aspect, the invention is a method of treating at least partial ureteral obstruction of a patient utilizing a ureteral stent. The stent comprises a proximal portion, a distal portion, and an elongated body portion configured to fit the ureter of the patient and defining a lumen. The stent further comprises an end-effector positioned at the proximal portion for retaining the proximal portion of the stent in the urinary bladder. A retention end-piece is disposed at the distal portion of the stent for retaining the distal portion in the renal pelvis. The method according to the invention includes the steps of inserting the stent into the urinary tract of patient, deploying the retention end-piece of the stent positioned at the proximal portion of the stent in the urinary bladder by inflation of a balloon, deploying the end-effector positioned at the distal portion of the stent in the renal pelvis of the kidney, facilitating urinary drainage from the distal portion of the stent located in the renal pelvis of the kidney to the proximal portion of the stent located in the urinary bladder, and finally deflating the balloon and removing the stent from the urinary tract of the patient.

In another aspect, the invention is a method of delivery of drugs or biologics into the urinary bladder from the contents of the balloon of the proximal end-effector.

BRIEF DESCRIPTION OF THE DRAWINGS

FIG. 2 illustrates an enlarged view of the end-effector positioned at the proximal portion of the stent and the pusher tube adjacent thereto according to one embodiment of the invention.

FIGS. 3A-3H illustrate various embodiments of a cross-section of the end-effector illustrated in FIG. 2, taken along line A-A.

FIG. 5A is a sectional view of one of the ureteral stent illustrated in FIG. 1A depicting the end-effector in a deflated state and the pusher tube adjacent thereto.

FIG. 5B is a plan view of the ureteral stent illustrated in FIG. 1A depicted the end-effector in an inflated state.

DETAILED DESCRIPTION

Figure 1A:
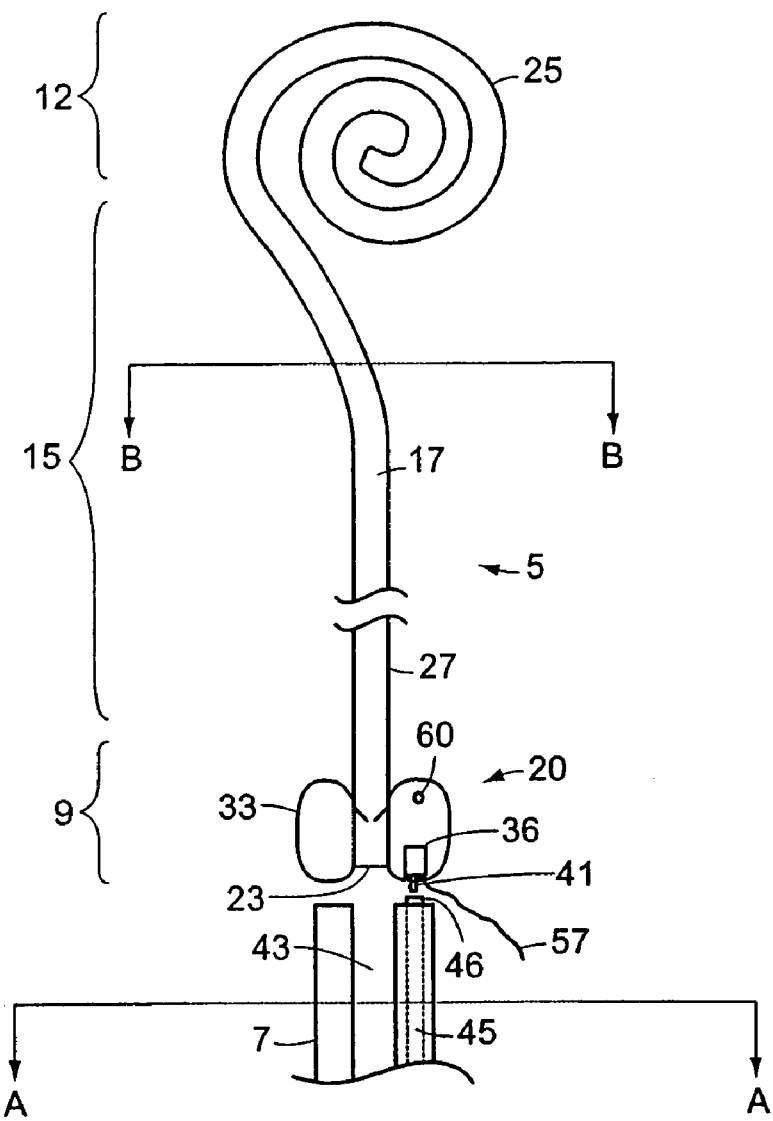
FIG. 1A is a plan view of a ureteral stent and a pusher tube according to one embodiment of the invention.

The invention generally concerns a drainage device that, when positioned within the ureter of a mammal, assists in reducing fluid retention by facilitating the drainage of urine from the kidney through the ureter and into the urinary bladder while simultaneously minimizing patient discomfort. A common feature of the invention is a proximal end-effector, including a balloon. Throughout the discussion of the illustrative embodiments, it is to be understood that in the figures, like reference characters generally refer to the same parts throughout different views.

Figure 1B:
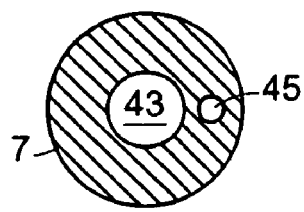
FIG. 1B is a cross-sectional view of the pusher tube illustrated in FIG. 1, taken along line A-A.
Figure 1C:
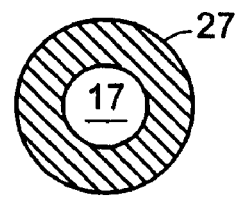
FIG. 1C is a cross-sectional view of the ureteral stent illustrated in FIG. 1, taken along line B-B.

Referring to FIGS. 1A-1C, a ureteral stent system comprising a ureteral stent 5 and pusher tube 7 according to the invention, in general, is shown. The stent 5 is suitable for use with the pusher tube 7 for implantation within the ureter of a patient, and includes a proximal portion 9, a distal portion 12, and an elongated body portion 15 defining a lumen 17 which extends between the proximal portion 9 and the distal portion 12. A proximal end-effector 20 is attached to a proximal end 23 of proximal portion 9 and a retention end-piece 25 is attached to distal portion 12. Both the stent 5 and the pusher tube 7 are dimensioned to fit the anatomical requirements of each application within the body.

Typically, in a ureteral application, the length of the elongated body portion 15 ranges between about 18 cm to 30 cm, preferably about 18 cm to 20 cm. The elongated body portion 15 has an outside diameter of at least about 1.6 mm to 3.3 mm, preferably 2 mm (or French size 6). The thickness of a wall 27 of the elongated body portion 15 is at least about 0.05 mm to 0.35 mm, and preferably about 0.2 mm.

A number of biomaterials are available for construction of the ureteral stent system according to the invention. The subset of biomaterials best suited for stent construction exhibit the following characteristics: high tensile strength, high retention coil strength, excellent biocompatibility and biodurability, excellent radiopacity or flouroscopic visibility, availability in varying durometers and a low resistance to passage. In a preferred embodiment, the stent 5 may be constructed from shape memory tubing, such as PERCUFLEX® (Boston Scientific Corporation, Natick, Mass.) C-FLEX® (Xomed-Trease, Inc.), FLEXIMA™, or other polymer material including polytetrafluoroethylene (PTFE), silicone polyurethane, polyurethane plastics, polyethylene plastics, and thermoplastics, for example.

Referring to FIG. 2, enlarged views of the proximal end-effector 20 and pusher tube 7 are depicted. As discussed further in FIG. 4, the proximal end-effector 20 is attached to proximal portion 9 and serves to retain the proximate portion 9 of stent 5 within the urinary bladder 30. In one embodiment, the proximal end-effector 20 completely surrounds the proximal portion 9 of stent 5. The proximal end-effector 20 may be integral with, or detachable from the proximal portion 9 of the stent 5. The proximal end-effector 20 comprises a balloon 33 and an end-effector valve 36 and may be constructed from materials with similar properties to the stent 5, but should be compliant with a high percentage of elongation such as, for example, silicone or latex. In one embodiment, the proximal end-effector 20 may be attached to proximal end 23 of proximal portion 9 and in other embodiments, the proximal portion 9 of stent 5 may be disposed through the proximal end-effector 20 such that the proximal end-effector 20 is located from between 0 and 10 mm from a proximal end 23 of the proximal portion 9 of stent 5.

Referring now to FIGS. 3A-3H, various embodiments and modes of attachment of the proximal end-effector 20 to proximal portion 9 are illustrated. For example, referring to FIG. 3A, the proximal end-effector 20 includes a balloon 33 surrounding the proximal portion 9 of the elongated body portion 15 of the stent 5. The wall 27 of the elongated body portion 15 may include one or more apertures between the lumen 17 and the interior of balloon 33 as shown in FIGS. 3B and 3C. In another embodiment, the proximal end-effector 20 includes a balloon 33 having an hour-glass shape in cross-section as illustrated in FIG. 3D. Referring to FIG. 3E, in another embodiment, the proximal end-effector 20, includes at least two balloons 33. In another embodiment, referring to FIG. 3F, the proximal end-effector 20 includes at least two balloons 33 having independent lumens, i.e., the lumens are not common. In yet another embodiment of the invention, illustrated in FIG. 3G, the proximal end-effector 20 includes a balloon 33 asymmetrically disposed on the external surface of the proximal portion 9 of the stent 5. In a further embodiment depicted in FIG. 3H, opposite sides of wall 27 are thinned to cause lumen 17 to be pinched off in response to a predetermined pressure transmitted by the fluid in balloon 33 during patient voiding. Other embodiments of the balloon 33 are also contemplated and the invention is not limited to the embodiments illustrated in FIGS. 3A-3H.

Referring to FIG. 2, in one embodiment, the proximal end-effector 20 further comprises a proximal lumen valve 39 disposed within the lumen 17 of the proximal portion 9 of the stent 5. The proximal lumen valve 39 serves to prevent or reduce reflux of urine back up the ureter due to retrograde pressure that occurs during patient voiding. The proximal lumen valve 39 may be, for example, a unidirectional or "duck-bill" type that permits fluid to flow only substantially in the distal to proximal direction.

Referring still to FIG. 2, the end-effector valve 36 may be, for example, a self-sealing valve or bi-directional valve. In one embodiment, the end-effector valve 36 comprises a valve inlet 41 for inflation and deflation of balloon 33 with a suitable biocompatible gas or biocompatible liquid. With continued reference to FIG. 2, the pusher tube 7 has two lumens, a primary pusher tube lumen 43 and an inflate lumen 45. A port 46 is disposed at one end of the inflate lumen 45 and engages valve inlet 41 of the end-effector valve 36 for delivery of a medium into balloon 33. Valve inlet 41 will open when engaged by port 46 of pusher tube 43 and valve 41 will close when port 46 is disengaged from valve inlet 41. The valve inlet 41 will also open by pulling deflate suture 57 to deflate balloon 33 and allow removal of stent 5. In another embodiment, a syringe may be used for inflation of balloon 33.

With continued reference to FIG. 2, the balloon 33 may be filled via the inflate lumen 45 of pusher tube 7 with a liquid pharmaceutical such as an anesthetic, an antipasmodic agent, an anti-cholinergic agent, chemotherapeutic agent, or agents for transfection of genes. In this embodiment, the balloon serves the dual function of retaining the proximal portion 9 of stent 5 within the urinary bladder 30 and acting as a reservoir for the controlled delivery of a pharmaceutical agent into the urinary bladder 30. The pharmaceutical agent contained within balloon 33 is released into the bladder 30 through various known means such as a small orifice 60, perforated through balloon 33 as illustrated in FIG. 2, or controlled release through valve inlet 41 of end-effector valve 36. In another embodiment, balloon 33 may contain a plurality of perforated orifices.

In a further embodiment, balloon 33 may be constructed from a semi-permeable membrane to effect the controlled released of the contents of balloon 33 into bladder 30 by diffusion, resulting from a pressure gradient between the inside of balloon 33 and bladder 30. The pharmaceutical agent may be continuously released at a known rate during the entire indwelling of stent 5 within the body of the patient. In a preferred embodiment a sufficient quantity of the agent should be retained in balloon 33 before removal of stent 5 to hold the proximal portion 9 of stent 5 comfortably within the urinary bladder 30. Any remaining portion of the pharmaceutical agent may be released during cystoscopic removal of stent 5 by pulling the deflate suture 57, illustrated in FIG. 2, which in turn, opens valve inlet 41 of end-effector valve 36. The surplus volume of the pharmaceutical agent is immediately flushed and drained from the urinary bladder 30 through the cystoscopic sheath.

Figure 4:
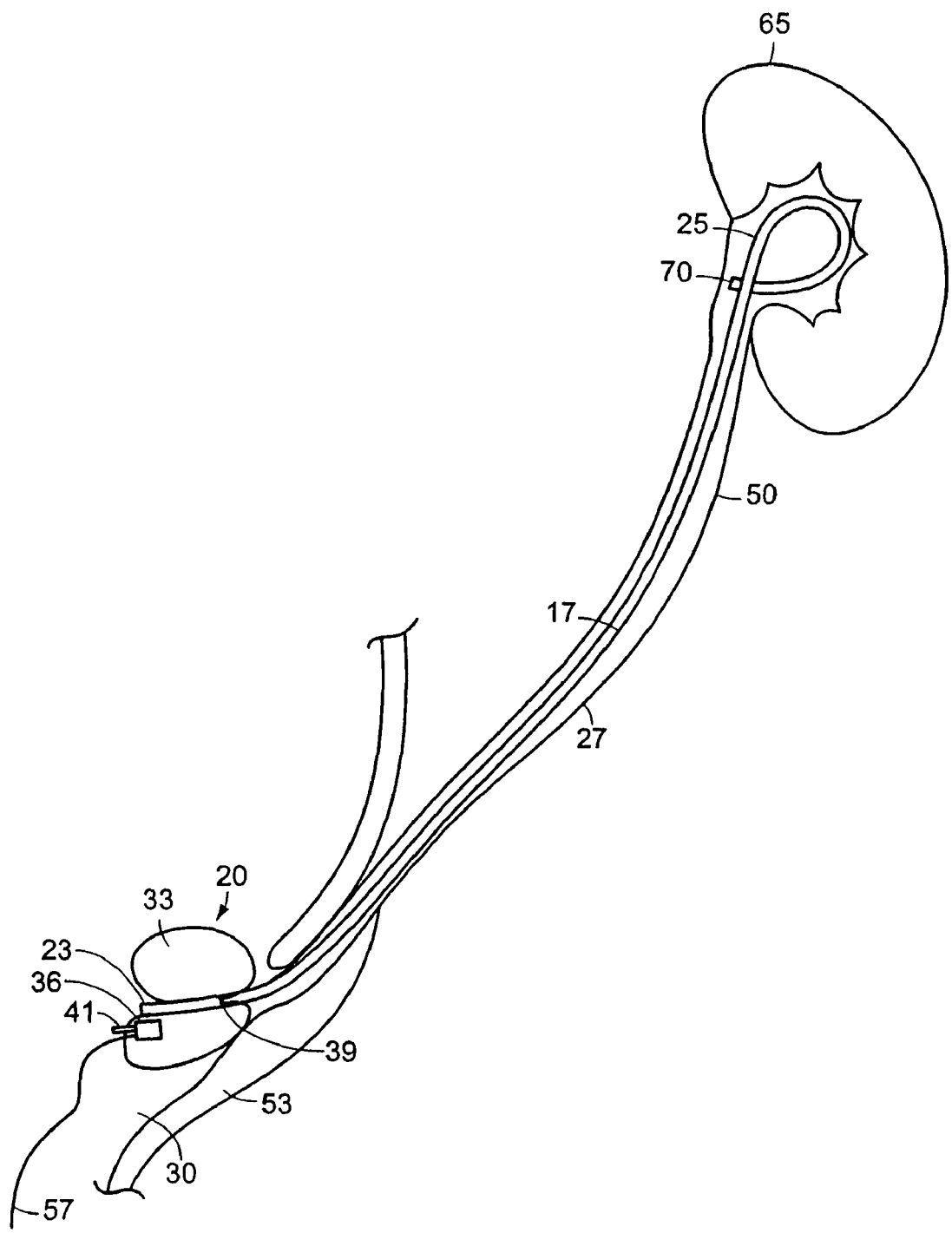
FIG. 4 illustrates a clinical application of the ureteral stent according to one embodiment of the invention.

Referring now to FIG. 4 a clinical application of ureteral stent 5 according to the invention is depicted. In one embodiment of the invention, pusher tube 7 is used to deliver the stent 5 through a cytoscope over a guide wire (not shown) and into the ureter 50. In another embodiment, stent 5 is introduced endoscopically without the use of pusher tube 7. As shown in FIG. 5A, before stent 5 is inserted into the body, the deflated balloon is substantially the same diameter in this deflated form as the proximal portion 9 of stent 5. After insertion into the body, the port 46 of the inflate lumen 45, is detachably coupled to the valve inlet 41 of end-effector valve 36 and a medium, such as, for example, saline, is introduced through the inflate lumen 45 to inflate balloon 33 to a suitable diameter, such as 3 to 10 mm, preferably 5 mm, for retention of the proximal portion 9 of stent 5 within the urinary bladder 30 as best seen in FIG. 5B.

Referring again to FIG. 4, once inflated, balloon 33 is positioned proximal to the bladder wall 53 thereby minimizing migration of stent 5 within the ureter 50 and maintaining the elongated body portion 15 in situ. For removal of stent 5, the deflate suture 57 of end-effector valve 36 is pulled by an operator, thereby opening the end-effector valve 36, dispensing the contents of balloon 33 into the urinary bladder 30, and restoring the diameter of balloon 33 to substantially the same diameter as the proximal portion 9 of stent 5. Further pulling of deflate suture 57 will remove stent 5 from the patient.

In one embodiment, with continued reference to FIG. 4, the lumen 17 of elongated body portion 15 of stent 5 is disposed through the center of balloon 33 without restriction to permit drainage of urine from the kidney 65 directly into the urinary bladder 30. The proximal lumen valve 39, such as a duck-bill or ball-type valve, is disposed within proximal portion 9 of stent 5 to further enhance the comfort of the stent 5 by preventing or reducing ureteral reflux during patient voiding.

In another embodiment, urine reflux is reduced without the use of a proximal lumen valve 39. In this embodiment, the wall 27 of the proximal portion 9 of the stent 5 surrounded by proximal end-effector 20, has a durometer, size, and configuration sufficient to permit the lumen 17 of this portion of the stent 5 to close by collapsing during voiding. For example, the thickness of wall 27 at the proximal portion 9 of stent 5 may be reduced, i.e., thinner relative to the thickness of the wall 27 of the other portions of the elongated body portion 15. The increase in pressure within the urinary bladder 30 during voiding is hydraulically transferred through the fluid medium of balloon 33 to the wall 27 of proximal portion 9. The reduction in the thickness of wall 27 in the proximal portion 9 and the greater surface area of wall 27 as compared to the cross sectional area of lumen 17 will cause lumen 17 to substantially collapse in response to a predetermined pressure increase such as voiding. Accordingly, the collapsibility of the proximal portion 9 during voiding serves to prevent or substantially reduce ureteral reflux during patient voiding. The collapsible wall 27 along the proximal portion 9 is constructed from one or more biocompatible plastics or polymers including, for example, polytetrafluoroethylene (PTFE), silicone, polyurethane, polyurethane plastics, polyethylene plastics, and thermoplastics. The thickness of the collapsible wall 27 in the proximal portion 9 of the stent 5 ranges from 0.05 to 1.0 mm, preferably less than 0.07 mm.

Figure 6A:
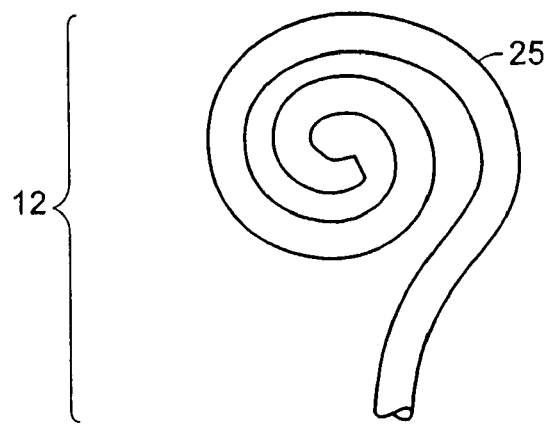
FIGS. 6A-6C illustrate various embodiments of the distal portion of the stent according to the invention.
Figure 6B:
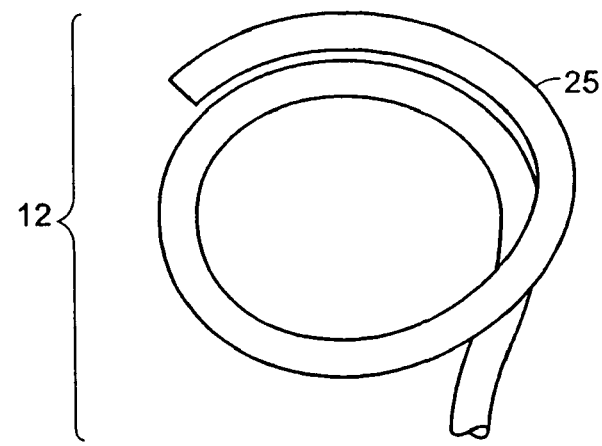
Figure 6C:
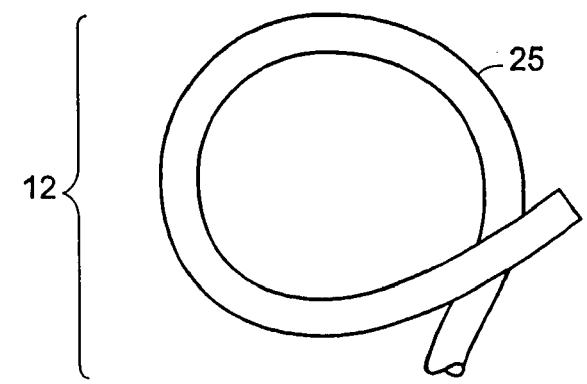

FIGS. 6A-6C, depict enlarged views of various embodiments of the retention end-piece 25 located at distal portion 12 of the ureter stent 5. The retention end-piece 25 is formed by bending distal portion 12 into a planar or substantially planar spiral configuration to retain the distal portion 12 of the stent 5 in the renal pelvis 70 of the kidney 65, as depicted in FIG. 4. In one embodiment, as shown in FIG. 6A, retention end-piece 25 is formed by shaping distal portion 12 into a planar spiral coil formed with a multiplicity of turns wound concentrically within the same plane. In another embodiment, as shown in FIG. 6B, retention end-piece 25 is formed by shaping distal portion 12 into a helical coil formed with at least one turn. FIG. 6C shows another embodiment of distal portion 9, wherein retention end-piece 40 comprises its smallest configuration having slightly over one complete spiral turn of distal portion 12.

It is will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the claims and their equivalents.

What is claimed is:

1. A medical device, comprising:
an elongate member having a sidewall defining a lumen, the sidewall including a proximal portion, a distal portion, and a body portion, the proximal portion of the sidewall being configured to be placed within a bladder of a patient, a first valve disposed within the lumen defined by the sidewall and configured to help prevent movement of fluid within the lumen defined by the sidewall from the bladder of the patient to a kidney of the patient;
a balloon coupled to the elongate member, the balloon including a reservoir for storing a fluid, the reservoir being fluidically isolated from the lumen defined by the elongate member, the balloon defining at least one orifice configured to controllably release a fluid stored within the balloon into the bladder of the patient; and
a second valve operatively coupled to the balloon configured to allow and prevent a flow of fluid into and out of the balloon to control the amount of fluid in the reservoir of the balloon to be released into the bladder of the patient, the second valve being disposed on the balloon such that the valve is disposed in the bladder of the patient when the balloon is disposed therein.

2. The medical device of claim 1, wherein the second valve is a uni-directional valve operatively coupled to an interior region of the balloon to control the flow of fluid into and out of the interior region of the balloon.

3. The medical device of claim 1, wherein the second valve is a self-sealing valve operatively coupled to an interior region of the balloon to control the flow of fluid into and out of the interior region of the balloon.

4. The medical device of claim 1, wherein the distal end portion of the sidewall is configured to help retain at least a portion of the elongate member within the kidney of the patient.

5. The medical device of claim 1, wherein the distal end portion of the sidewall includes a substantially spiral configuration.

6. The medical device of claim 1, wherein the distal end portion of the sidewall includes a substantially helical coil configuration.

7. The medical device of claim 1, wherein a proximal end of the medical device and a distal end of the medical device are configured to be disposed within a body of the patient.

8. The medical device of claim 1, wherein a proximal end of the balloon is disposed proximal to a proximal end of the sidewall when the proximal portion of the sidewall is disposed within the bladder of the patient.

9. The medical device of claim 1, wherein the proximal portion of the sidewall has a first thickness, the body portion of the sidewall having a second thickness greater than the first thickness.

10. A medical device, comprising:
a sidewall defining a lumen and having a proximal portion, a distal portion, and a medial portion; and
a balloon coupled to the proximal portion of the sidewall such that a proximal end of the sidewall is disposed between a proximal end portion of the balloon and a distal end portion of the balloon,
the proximal portion of the sidewall having a first wall thickness and the medial portion of the sidewall have a second thickness, greater than the first thickness, such that the proximal portion of the sidewall can be moved between a relaxed configuration in which the portion of the lumen defined by the proximal portion of the sidewall is opened and a collapsed configuration in which the portion of the lumen is at least partially closed,
the balloon containing a volume of fluid that remains the same when the proximal portion of the sidewall is in both the relaxed configuration and the collapsed configuration, the proximal portion of the sidewall assuming its collapsed configuration in response to a pressure exerted on the balloon and transferred to the proximal portion of the sidewall through the fluid contained within the balloon.

11. The medical device of claim 10, wherein the balloon substantially surrounds the proximal portion of the sidewall.

12. The medical device of claim 10, wherein the balloon is configured to be placed in a bladder of a patient, the balloon being configured to help retain at least a portion of the sidewall within the bladder of the patient.

13. The medical device of claim 10, wherein the distal portion of the sidewall is configured to be disposed within a kidney of a patient, the distal portion including a substantially spiral configuration.

14. The medical device of claim 10, wherein the distal portion of the sidewall is configured to be disposed within a kidney of a patient, the distal portion including a substantially helical coil portion.

15. The medical device of claim 10, further comprising:
a valve being operatively coupled to an interior region of the balloon to control the flow of fluid into and out of the interior region of the balloon.

16. The medical device of claim 10, further comprising:
a valve being operatively coupled to an interior region of the balloon to control the flow of fluid into and out of the interior region of the balloon, the valve is configured to be placed in a urinary tract of a patient.

17. The medical device of claim 10, wherein the pressure is substantially equal to a pressure within a bladder of the patient when a patient urinates.

18. The medical device of claim 10, wherein a proximal end of the medical device and a distal end of the medical device are configured to be disposed within a body of a patient.

19. The medical device of claim 10, wherein a proximal end of the balloon is proximal to a proximal end of the sidewall when the medical device is disposed within a body of a patient.

20. The medical device of claim 10, further comprising:
a valve being operatively coupled to an interior region of the balloon to control the flow of fluid into and out of the interior region of the balloon, the valve being disposed on a surface of the balloon and being configured to be placed in a urinary tract of a patient.

21. A medical device, comprising:
an elongate member having a sidewall defining a lumen, the sidewall including a proximal end configured to be placed within a bladder of a patient;
a balloon coupled to the elongate member, the balloon including a reservoir for storing a fluid, the reservoir being fluidically isolated from the lumen defined by the sidewall, the balloon being disposed such that the proximal end of the sidewall is disposed between a first end portion and a second end portion of the balloon when the medical device is disposed within a urinary tract of a patient;
a first valve operatively coupled to the balloon, the first valve being in fluid communication with the reservoir and configured to allow and prevent a flow of fluid into and out of the reservoir, the first valve being configured to be placed in the urinary tract of the patient; and
a second valve disposed within the lumen defined by the sidewall.

22. The medical device of claim 21, wherein a distal end portion of the sidewall includes a substantially helical coil configuration.

23. The medical device of claim 21, wherein the balloon substantially surrounds the proximal end of the sidewall.

24. The medical device of claim 21, further comprising:
the second valve being unidirectional such that fluid can substantially flow through the lumen in a proximal direction, the second valve being configured to substantially prevent fluid in the lumen to flow in a distal direction.

25. The medical device of claim 21, wherein the balloon defines at least one orifice through which a fluid within the reservoir can be released into the urinary tract of the patient.

* * * * *